(12) United States Patent
Chuhran

(10) Patent No.: US 6,682,755 B1
(45) Date of Patent: Jan. 27, 2004

(54) FOOD ENERGY INHIBITOR FOR ANTS

(76) Inventor: James E. Chuhran, 7676 Dolphin, Detroit, MI (US) 48239

(*) Notice: Subject to any disclaimer, the term of this patent is extended or adjusted under 35 U.S.C. 154(b) by 0 days.

(21) Appl. No.: 09/695,470

(22) Filed: Oct. 24, 2000

Related U.S. Application Data

(63) Continuation-in-part of application No. 09/197,548, filed on Nov. 23, 1998, now Pat. No. 6,136,340, which is a continuation-in-part of application No. 08/661,079, filed on Jun. 10, 1996, now abandoned, which is a continuation-in-part of application No. 08/500,613, filed on Jul. 11, 1995, now abandoned.

(51) Int. Cl.⁷ .................. A61K 47/00; A01N 25/00; A01N 25/08; A01N 25/34
(52) U.S. Cl. .................. 424/439; 424/403; 424/405; 424/408; 424/410
(58) Field of Search .................. 424/439, 405, 424/403, 408, 410

(56) References Cited

U.S. PATENT DOCUMENTS

| | | | | |
|---|---|---|---|---|
| 4,992,275 A | * | 2/1991 | Lush | 424/408 |
| 5,186,935 A | * | 2/1993 | Tucker | 424/410 |
| 6,136,340 A | * | 10/2000 | Chuhran | 424/439 |

* cited by examiner

*Primary Examiner*—Thurman K. Page
*Assistant Examiner*—S. Howard
(74) *Attorney, Agent, or Firm*—Charles W. Chandler

(57) ABSTRACT

A method for controlling insects, such as ants, comprising orally administering to the insects an effective amount of a food energy inhibitor consisting essentially of cellulose spent grain in a particulate form, mixed with an attractant without the addition of an insecticide, pesticide or poison.

5 Claims, No Drawings

FOOD ENERGY INHIBITOR FOR ANTS

CROSS-REFERENCE TO RELATED APPLICATION

This application is a continuation-in-part of Ser. No. 09/197,548 filed on Nov. 23, 1998 which is U.S. Pat. No. 6,136,340 issued Oct. 24, 2000 for "Food Energy Inhibitor for Rodents" which was a continuation-in-part of Ser. No. 08/661,079 filed Jun. 10, 1996 for "Toxicant-Free Rodent Exterminator", now abandoned, which in turn was a continuation-in-part of application Ser. No. 08/500,613, filed Jul. 11, 1995, for "Toxicant-Free Rodent Exterminator", now abandoned.

BACKGROUND OF THE INVENTION

Many products are available for controlling insects, such as ants. Such products usually employ an inert substance combined with an insecticide. However, products with a toxicant may only be used in carefully selected areas to avoid contaminating food supplies, water supplies, domestic animals and people. As used in this specification, the word "toxicant" is intended to mean a poisonous additive.

The conventional programs for managing these pests attempt to reduce their population to tolerable levels. Such elimination methods include baiting, mound drenching and broadcasting of contact insecticide having a toxic component.

I have found that using a food energy inhibitor consisting of a cellulose spent grain, mixed with an attractant, without the addition of a pesticide or poison is effective, but safe to humans, for managing selective rodents such as rats and mice. Such a product and method is disclosed in my co-pending patent application Ser. No. 09/197,548. The product is notable because it is harmless to other animals, pets, children and adults, regardless of how it is applied to rodent infested areas.

SUMMARY OF THE INVENTION

The preferred embodiment of the invention is a cellulose product used for controlling insects, such as ants, without using a toxic component. It includes an active ingredient and an attractant/binder. The ants receive no nourishment from the cellulose and die from lack of energy as the product absorbs the body juices. The insects become disoriented and die. In some cases, the ants transport the product into the nest where it is believed the reproductive ants consume the product and die.

The formula of the preferred product is:

| Material | Percentage | Purpose |
| --- | --- | --- |
| Cellulose | 99% | Active Ingredient |
| Molasses | 1% | Attractant/Binder |

CELLULOSE

Definition: The major component of the food energy inhibitor; chief constituent of cellulose particles of plants, wood, hemp, paper, etc., a carbohydrate.

| Types of Cellulose: | Corn Cob | Wheat |
| --- | --- | --- |
| | Peanut Shells | Bagasse |
| | Hops | Bran |
| | Beet Pulp | Barley |
| | Rice Germ | Whole Oats/Oat Bran |
| | Rye | Buckwheat |

Molasses is used as an attractant/binder because, after reviewing the literature, many attractants also provide binding capability. For example, cane molasses is used extensively in the baking industry as a shortening agent. It improves the flavor, provides cohesion and improves the "texture" of the foodstuff.

BINDER

Definition: an agent used to improve the consistency, cohesiveness, and texture of the preferred food energy inhibitor, a substance to improve the palatability of the food energy inhibitor to insects.

| General Category: | Fats, Oils, Proteins | |
| --- | --- | --- |
| Examples: | Peanut Oil | Soybean Oil |
| | Cottonseed Oil | Corn Oil |
| | Vegetable Oil | Coconut Oil |
| | Gluten | Lard |
| | Tallow | Nut Butter (i.e. peanut) |

Oils are used extensively as shortening; in salad oils, livestock feed, soaps, paints and lubricants. Glutens are proteins derived from grains; used in the preparation of foods, especially cereals; used in cattle feed and in making adhesives.

ATTRACTANT

Definition: A substance used to attract insects such as ants to the bait. The purpose of the attractant is to overcome "bait shyness" and encourage the consumption of the food energy inhibitor.

| Examples: | Maple Sugar | Beet Molasses |
| --- | --- | --- |
| | Cottonseed Meal | Cane Molasses |
| | Cane Syrup | Honey |
| | Corn Syrup | Bone Meal |
| | Malt Sugar | Beer/Ales |

Cane molasses is used extensively in baked goods and candies and is a major raw material for livestock feed and as a binder. Cane syrup and corn syrup are used extensively in baked goods, candies act as binders.

The mechanism of action for the food energy inhibitor is to encourage the ant to consume the product (the purpose of the attractant). Grains are the seed-like fruit of certain species of the grass family such as rice, wheat, corn, oats, barley, and rye. The plants that produce these fruits are also called grains.

Using corn as an example, the corn plant is actually a grass and the kernels themselves are grains. The fiber in corn is soluble; yet, oats and barley, which are in the same species as corn, contain fiber that is insoluble. The fiber in corn passes through the GI tract unchanged where the fiber in oats and bran are affected. The solubility of the grain used in the food energy inhibitor can effect efficacy.

Many factors affect the efficacy of products used to control insects. For instance, ants do not possess the morphological or physiological mechanism to regurgitate food as do dogs, cats and other animals. This is one reason why ants are so susceptible to poisons.

However, if the ants continue to consume a non-nutritional substance (cellulose), in their crop, their energy level puts them in a "coma", without using a primary or secondary active toxic.

The preferred embodiment of the invention comprises pellets formed of crushed spent grain such as corncobs, and an insect attractant such as a sugar sweetener or a protein.

Another object of the invention is to provide a toxicant-free product for controlling insects, such as ants, in the form of pulverized or ground-up spent grain such as corncobs that are dried and sprinkled in the area where the ants are present.

Some advantages of the invention are that the product can be safely used indoors, outdoors, in the home, around food and in the fields.

In one form of the invention, the material will not dissolve in water. The product can be dispensed by hand without fear of toxic chemical exposure. It is believed to be completely non-toxic to animals other than rodents such as rats and mice. The product will not contaminate a drinking water supply, will not harm fish, birds or wild life, will not cause any harmful effects if swallowed or absorbed through the skin, will not harm children or pets, and can be safely eaten by domestic animals and livestock.

In the preferred form of the invention, the product is applied in the form of small pellets, such as U.S. 40 mesh, using a shaker. Tests indicate that the product is selective because it is not harmful to animals, other than rats and mice, and insects such as ants.

The grain is milled to separate the floury endosperm from the bran and germ. The milled grain is then rolled to extract the oil from the germ. The remaining product is a non-nutritional by-product known in the industry as "spent grain."

The spent grain is then passed through a drying process and aerated to achieve a moisture content ranging from 7%–9%. Another rolling and aeration process using double rollers removes any remaining colloidal minerals to produce all natural cellulose.

The cellulose in a workable size particle is then mixed with the attractant and binding substance and pelletized to ¼ to ⅜ inch in length.

The product is dried to a moisture level of preferably 7%–9%, which causes the product to absorb the moisture from the insect.

The attractant is selected according to what is readily available and what the ants are accustomed to eating. It may range from molasses, beer, blood, shrimp, nuts, fish, beets, dry or liquid.

The pellets may be used in both urban and rural settings, around buildings, including homes, in agricultural settings, such as barns, grain bins, and animal quarters.

DESCRIPTION OF THE PREFERRED EMBODIMENT

The preferred composition is produced by preparing a substantially dry base of a cellulose such as crushed corncobs, without kernels, and 1% by weight of molasses as an insect attractant and binder. The kernels are first removed from the corncobs in a mill. The core of the corncobs is then drilled to recover a powder used for other purposes. The remaining rings are crushed to a U.S. sieve size of 40 so as to be easily ingested by the insect.

The crushed corncobs are dried to a 7%–9% level of moisture, by weight. The dried particles are then mixed with molasses in a ribbon mixer. Some steam is applied to caramelize the molasses. The mixture is formed into pellets in a pelletizing mill, such as a Scott Pellet Mill. The molasses acts both as a binder and as a sweet attractant.

The pellets are distributed in locations where the insects are active. Over a period of several days, ants die after consuming the pellets.

When the corncobs are crushed in a finer powder-like form than that used for rodents, with or without an attractant, the powder can be distributed in the vicinity where ants are present. Tests indicate that the dried cellulose powder, without the attractant, is effective on such ants as carpenter ants, fire ants and termites. The material is spread around the anthill so as to be in the ants' path. The ants die upon ingesting the powder. The cause of death is physical, not toxicological.

The pellets may be coated with paraffin or other coating to protect the composition from contact with water.

The pellets are placed in areas where evidence of ant activity exists. The pellets are replenished as needed until signs of ant activity ceases.

Tests have been successfully conducted with carpenter ants (Campontus pennsylvanicus), acrobatic ants (crematogaster spp.), odorous house ants (Tapinoma sessile), pavement ants (tetramorium caespitum) and fire ants (solenopsis spp.).

The following example illustrates the use of the preferred embodiment of the invention.

On September 16$^{th}$, Carpenter ants (Campontus pennsylvanicus) were observed at a residence. Repeated efforts by two different State of Michigan certified technicians to eliminate the problem were unsatisfactory. The problem was unique in that the worker ants moved from somewhere in the roof of the residence to a Hummingbird feeder fastened to the home by a slightly concave 12" long bracket. The ants had no need to forage except to the feeder. This likely precluded efficacy using conventional treatments with chemicals to the exterior of the building.

The sugar water was removed from the container, which was not dried. Two ounces of Delmar Monitor (an example of the invention) were placed in the feeder, which was then replaced to its original position. Twelve pellets were also placed on the bracket in the path of the worker ants. Worker ants were observed to stop en route to the feeder and began feeding on the Delmar pellets. This activity was observed for approximately thirty minutes. No worker ants attempted to pass the Delmar pellets to their usual feeding station during that period, although 57 worker ants were counted. (Temperature 72 Degrees Fahrenheit)

On September 23$^{rd}$, only one pellet remained at the site. The feeder was examined and observed that moisture had swollen the Delmar pellets. The eleven missing Delmar pellets were replaced and the site observed for 40 minutes. No worker ants were sighted in 40 minutes on this date. (Temperature 79 Degrees Fahrenheit)

Telephone conversation four days after the initial treatment with the resident indicated that he had not seen any worker ants. Later the resident advised that he had not seen anymore worker ants since the second visit. On October 27$^{th}$, the resident left the following message "the ants are all gone."

No other treatments were made during the study and even though conditions were conducive to worker ant activity during the period, no activity occurred after the September 23$^{rd}$ treatment.

Approximately, one month later there was still no activity, hence one must conclude in this instance and under these circumstances, the ant colony was killed with Delmar monitor.

What is claimed is:

1. A method for killing insects, comprising the steps of:

milling grain to separate floury endosperm from the bran and germ;

rolling the grain to extract oil from the germ to form a cellulose spent grain;

drying and aerating the cellulose spent grain to a moisture content of less than 10%;

mixing the cellulose spent grain with a binding substance and a toxicant-free insect attractant to form a food energy inhibitor, pelletizing the food energy inhibitor to a size suitable for ingestion by insects;

drying the food energy inhibitor pellets to a moisture level of 7% to 9%; and orally administering to the insects an effective amount of the food energy inhibitor pellets without adding an insecticide, pesticide or poison.

2. A method for killing insects comprising the steps of:

crushing cellulose spent grain to a size that can be ingested by an insect;

orally administering to the insects an effective amount of the crushed cellulose spent grain without the addition of an insecticide, pesticide or poison.

3. A method for killing insects, comprising the steps of:

milling corncobs to separate the kernels from the cobs;

rolling the cobs to form a cellulose spent grain;

drying and aerating the cellulose spent grain to a moisture content of less than 10%;

mixing the cellulose spent grain with a binding substance and a toxicant-free insect attractant to form a food energy inhibitor;

pelletizing the food energy inhibitor to a size suitable for ingestion by insects;

drying the food energy inhibitor pellets to a moisture level of 7% to 9%; and orally administering to the insects an effective amount of the food energy inhibitor pellets without adding an insecticide, pesticide or poison.

4. A method for making a food energy inhibitor for insects, comprising:

milling grain to separate floury endosperm from the grain and germ;

rolling the grain to extract oil from the germ to form a spent grain;

drying and aerating the cellulose spent grain to a moisture content of less than 10% by weight;

mixing the cellulose spent grain with a binding substance and a toxicant-free insect attractant to form a food energy inhibitor;

pelletizing the food energy inhibitor to a size suitable for ingestion by insects; and drying the food energy inhibitor to a moisture level of 7% to 9%.

5. A method for killing insects, comprising the steps of:

orally administering to the insects an effective amount of a food energy inhibitor consisting essentially of toxicant-free corncobs crushed to a size suitable for ingesting by insects, and mixed with a toxicant-free attractant.

* * * * *